US012650437B2

(12) United States Patent
Verbruggen et al.

(10) Patent No.: US 12,650,437 B2
(45) Date of Patent: Jun. 9, 2026

(54) FVIII INHIBITOR ASSAY

(71) Applicant: Technoclone Herstellung von Diagnostika und Arzneimitteln GmbH, Vienna (AT)

(72) Inventors: Hubertus Wilhelmus Verbruggen, Vienna (AT); Nikolaus Binder, Vienna (AT)

(73) Assignee: Technoclone Herstellung von Diagnostika und Arzneimitteln GmbH, Vienna (AT)

( * ) Notice: Subject to any disclaimer, the term of this patent is extended or adjusted under 35 U.S.C. 154(b) by 547 days.

(21) Appl. No.: 18/337,617

(22) Filed: Jun. 20, 2023

(65) Prior Publication Data

US 2023/0417776 A1      Dec. 28, 2023

(30) Foreign Application Priority Data

Jun. 23, 2022    (EP) ..................................... 22180750

(51) Int. Cl.
 *G01N 33/86* (2006.01)
(52) U.S. Cl.
 CPC ....... *G01N 33/86* (2013.01); *G01N 2333/755* (2013.01)
(58) Field of Classification Search
 CPC ......................... G01N 33/86; G01N 2333/755
 See application file for complete search history.

(56) References Cited

U.S. PATENT DOCUMENTS

2009/0053297 A1* 2/2009 Balu-Iyer ............... A61K 31/74
                                                      424/78.08
2009/0215070 A1* 8/2009 Parhami-Seren ...... C07K 16/40
                                                      435/7.1

OTHER PUBLICATIONS

Extended European Search Report issued in European Patent Application No. 22180750.6, dated Nov. 25, 2022.
Verbruggen, B. et al., "Diagnosis and quantification of factor VIII inhibitors," *Haemophilia*, 16 (2010): 20-24.
Verbruggen, B. et al., "Proof of principle of a fast and fully automated FVIII functional inhibitor test," [abstract]. https://abstracts.isth.org/abstract/proof-of-principle-of-a-fast-andfully-automated-fviii-functional-inhibitor-test/. Accessed Nov. 13, 2022.
Verbruggen, B. et al., "The Type of Factor VIII Deficient Plasma Used Influences the.Performance of the Nijmegen Modification of the Bethesda Assay for Factor VIII Inhibitors," *Thromb Haemost.*, 86 (2001): 1435-1439.

* cited by examiner

*Primary Examiner* — Jennifer Wecker
*Assistant Examiner* — Tracy Ching-Tian Colena
(74) *Attorney, Agent, or Firm* — pH IP Law

(57) ABSTRACT

The present invention relates to an improved method for determining the amount of FVIII inhibitors in a patient sample, comprising the provision of a patient plasma sample, a normal pool plasma samples, and a control plasma sample which is FVIII/VWF deficient, inactivating all clotting factors present in the samples, addition of recombinant FVIII (rFVIII) to the control plasma sample, combination of the patient plasma sample with the control plasma sample with rFVIII to obtain a test mixture, and of the normal plasma pool sample with the control plasma sample with rFVIII to obtain a control mixture, incubation of the test mixture and the control mixture for less than 30 minutes, and analyzing the mixtures for residual rFVIII activity in the absence of VWF.

17 Claims, 1 Drawing Sheet

Nijmegen assay

Heated patient plasma

Buffered normal pool plasma pH 7.4

Heated control plasma (factor VIII deficient plasma)

Test mixture    50/50 mix    Control mixture

Incubate
2 h @ 37°C

Remaining factor activity assay
In test- and control mixture

Calculate residual factor activity

Calculate inhibitor units (NBU mL$^{-1}$)

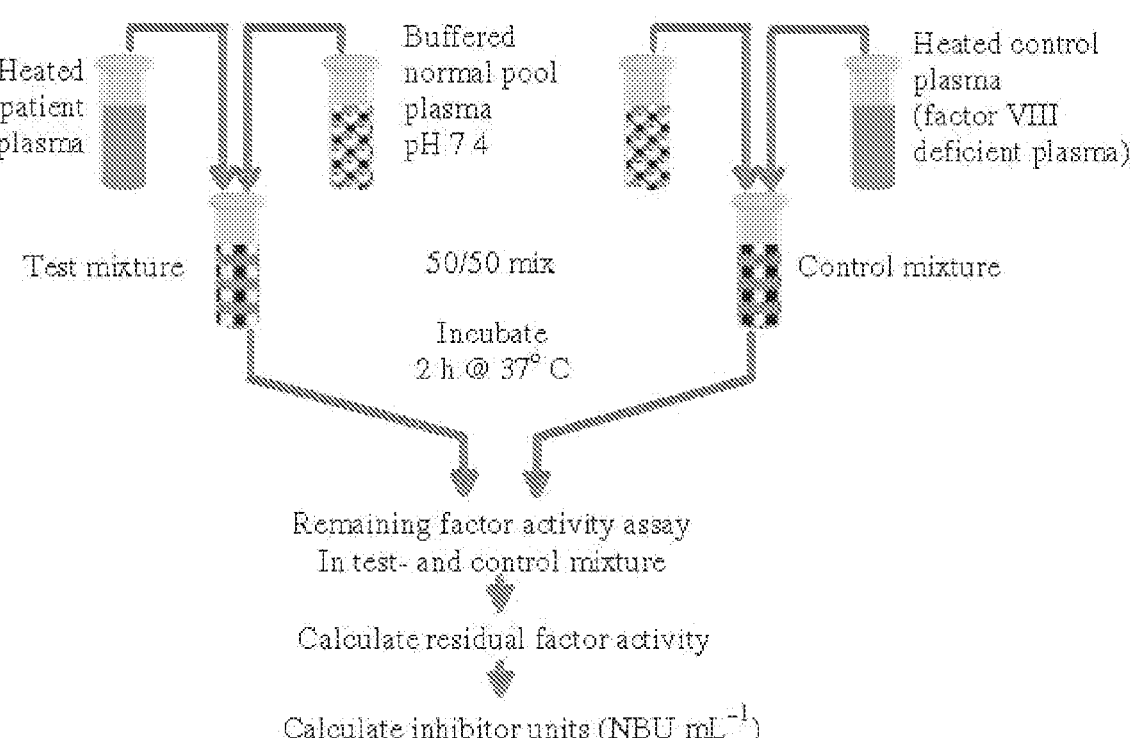

FVIII INHIBITOR ASSAY

CROSS-REFERENCE TO RELATED APPLICATIONS

This application claims priority to and the benefit of European Patent Application No. 22180750.6, filed Jun. 23, 2022, and entitled "FVIII FUNCTIONAL INHIBITOR TEST," which is incorporated herein by reference in its entirety.

FIELD

The present invention relates to the field of factor VIII inhibitor determination.

BACKGROUND

Inhibitors against the clotting factor VIII (FVIII) in hemophiliacs are a serious problem arising in 5-20% of patients treated with FVIII replacement therapy. All FVIII inhibitor assays are based on a universal method of measuring the decrease of clotting factor activity in a mixture of an exogenous source of the clotting factor, e.g., normal pooled plasma, and the putative inhibitor plasma in a certain time period. A reference measurement needs to be performed with the same method substituting the patient plasma by a control plasma sample that does not contain an inhibitor. Residual FVIIII activities in the assay mixtures are measured by one-stage-based clotting assays (Verbruggen B., Haemophilia 2010, 16, 20-24).

The schematic methodology of the Nijmegen-Bethesda assay for quantification of inhibitors is shown in FIG. 1. Patient plasma and FVIII-deficient control plasma are heated for at least 1.5 h to inactivate all clotting factors. Heated test plasma and also FVIII-deficient control plasma are mixed with equal volumes of buffered normal pooled plasma and incubated for 2 h at 37° C. Subsequently, the remaining FVIII activity in both test- and control mixtures is determined (Verbruggen, 2010).

The Nijmegen-Bethesda assay requires 2-hours incubation of test sample/FVIII-source mixture because of slow FVIII inactivation. Said extended incubation time results in non-specific FVIII inactivation, that, together with complicated liquid handling, may contribute to the considerable variability (CV:30-40%) seen in inter-laboratory surveys (e.g., ECAT, UKNEQAS).

Therefore, there is still the need for an improved method for reliable determination of FVIII inhibitors in patient samples.

SUMMARY

It is the object of the present invention to provide an improved method for determining FVIII inhibitors in patient samples. The object is solved by the subject-matter of the present invention.

Surprisingly it has been found that testing in a von Willebrand Factor (VWF)-free assay matrix using recombinant (r)FVIII can dramatically lower incubation time that, together with full automation, will substantially improve standardization of the FVIII inhibitor assay.

According to the invention, there is provided a method for testing for FVIII inhibitors in a patient sample, the method comprising the following steps:
   a. providing a previously obtained patient plasma sample or obtaining a patient plasma sample, b. providing buffered normal pool plasma samples,
   c. providing a control plasma sample which is FVIII/VWF deficient,
   d. heat treatment of the samples of step a) to c),
   e. adding recombinant FVIII (rFVIII) to the control plasma sample,
   f. combining the patient plasma sample with a control plasma sample with rFVIII to obtain a test mixture,
   g. combining a normal plasma pool sample and the control plasma sample with rFVIII to obtain a control mixture,
   h. incubating the test mixture and the control mixture for less than 30 minutes, and
   i. analyzing the mixtures for residual rFVIII activity in the absence of VWF.

The method is carried out in the absence of VWF. Thus, no substitution of purified VWF in the VWF-free control plasma sample or the FVIII depleted plasma for FVIII determination is required.

According to one embodiment of the invention, the incubation step is carried out for about 15 minutes, or for about 10 minutes, or for about 5 minutes.

A further embodiment relates to the method as described herein, wherein the incubation step is carried out at a temperature of about 37° C.

A further embodiment relates to the method as described herein, wherein the normal pool plasma and the control plasma are replaced with a buffered agent.

According to one embodiment of the invention the patient plasma sample is pre-diluted with a buffer agent. The buffer agent may be for example an imidazole buffer, owren's veronal buffer or a saline solution.

A further embodiment relates to the method as described herein, wherein the incubated samples are diluted in the range of 1:20, 1:10, or 1:5.

One embodiment of the invention relates to the method as described herein, wherein the residual rFVIII activity is determined by a clotting assay or a chromogenic assay. The clotting assay is for example an activated partial thromboplastin time assay (APTT).

One embodiment of the invention relates to an automated method for determining FVIII inhibitors. For example, the heat-treated samples as described herein are loaded on a coagulation analyzer.

The automated process comprises the following sequential steps:
   a. providing heat-treated samples of a patient plasma, of a normal pool plasma, and of a control plasma,
   b. adding rFVIII to the heat-treated control plasma sample,
   c. optionally pre-diluting the heat-treated patient plasma sample,
   d. combining the patient plasma sample and a control plasma sample with rFVIII to obtain a test mixture,
   e. combining the normal pool plasma sample and a control plasma sample with rFVIII to obtain a control mixture,
   f. incubating the test mixture and the control mixture for about 5, 10, or 15 minutes, and
   g. analyzing the mixtures for residual rFVIII activity in the absence of VWF.

According to one embodiment of the invention, the control plasma sample is devoid of von Willebrand factor (VWF). According to the invention, no substitution of VWF in the VWF free control plasma is required.

A further embodiment relates to the method as described herein, wherein 1.0 IU/mL rFVIII is added to the control plasma sample.

BRIEF DESCRIPTION OF DRAWINGS

FIG. 1 shows the schematic methodology of the Nijmegen-Bethesda assay for quantification of FVIII inhibitors.

DESCRIPTION

The present invention provides an improved method for testing for FVIII inhibitors in a patient sample. The currently used Bethesda or Nijmegen assay requires incubation for 2 h of test sample/FVIII-source mixture because of slow FVIII inactivation, due to its reversible binding to von Willebrand Factor (VWF) delaying inhibitor action.

The FVIII inhibitor assay is rather complicated and includes critical analytical stages and variables that need careful handling to get reliable results. The effect of incubation time and temperature on the measured inhibitor titer is essential. Verbruggen (2010) showed that at 37° C. an optimal inhibitor titer is reached after 120 minutes, whereas incubation times more than 180 min resulted in a marked decrease of FVIII activity is noticed even in the control sample.

Standard- and control samples for the FVIII inhibitor assay are not yet available. Intra-laboratory day-to day quality assessment can be performed by assaying negative and positive inhibitor samples that are stored at –80° C. Inter-laboratory surveys of FVIII inhibitor assays have been organized since 2005 by the European Concerted Action on Thrombophilia Foundation (ECAT). The results of the survey of ECAT showed a rather high inter-laboratory coefficient of variation of about 30% for the Nijmegen assay (Verbruggen, 2010).

Surprisingly it has been found that testing in a VWF-free assay matrix using recombinant (r)FVIII can dramatically lower incubation time resulting in a substantially improve FVIII inhibitor assay.

According to the invention, the method for determining FVIII inhibitors in a patient sample comprises the provision of a previously obtained patient plasma sample and of a control plasma sample which is FVIII/VWF deficient.

Both samples are subjected to a heat treatment in order to inactivate all clotting factors in the samples.

A determined amount of recombinant FVIII (rFVIII) is added to the patient plasma sample and to the control plasma sample after the heat inactivation step. The rFVIII may be a rFVIII of first, second, third or fourth generation, such as for example RECOMBINATE®, HELIXATE®, KOGENA-TEe®, ADVATE®, KOVALTRY®, REFACTO®, XYN-THA®, NOVOEIGHT®, NUWIQ®, ADYNOVATE®, ELOCTATE®, AFSTYLA®, or the like.

According to the invention, the patient plasma sample is mixed with control plasma comprising rFVIII to obtain a test mixture. The normal pool plasma is mixed in a like manner with control plasma likewise comprising rFVIII to obtain a control mixture. Thus, the test mixture and the control mixture both contain the same amount of rFVIII.

Verbruggen (2010) describes that the type of FVIII-deficient plasma used as control sample and as substrate plasma in the residual FVIII activity assay greatly influences the inhibitor test results. Inhibitor titers derived from assays with VWF-free immunodepleted FVIII-deficient plasma as control sample and as substrate plasma in the FVIII assay were 30-50% lower as compared with titers of assay using VWF containing deficient plasma due to the stabilizing effect of VWF. Substituting purified VWF in the VWF-free substrate plasma restored the inhibitor titer. Thus, Verbruggen (2010) strongly recommended to use VWF-containing FVIII-deficient plasma for a reliable assay set up.

In contrast to the state-of-the-art Nijmegen assay, the mixtures according to the invention are incubated for less than 30 minutes. Due to the use of rFVIII there is no need to have VWF as a stabilizing factor in the sample's matrices. For the VWF-free samples, the incubation time can be reduced to 30, 25, 20, 15, 10 or even to 5 minutes.

Thereafter, the residual rFVIII activity is determined in the test mixture and the control mixture.

The residual rFVIII activity is defined as the relative percentage rFVIII activity of the test mixture compared with the control mixture. One Nijmegen-Bethesda unit (NBU) is defined as that amount of inhibitor that results in 50% residual rFVIII activity. Inhibitor activity of patient plasma is read in NBU/mL from a logarithmic plot representing the correlation between residual rFVIII activity (logarithmic) and inhibitor activity (linear). The regression line is fully defined by 100% residual rFVIII activity with 0 NBU/mL inhibitor and 50% residual rFVIII with 1 NBU/mL. Dose response curves of test plasma need to show parallelism with the calibration curve.

The use of rFVIII allows for standardization of the patient sample and the control sample, resulting in an improved FVIII inhibitor assay. Additionally, due to the heat treatment, all samples are devoid of active VWF, and the incubation time of the test mixture and the control mixture is significantly reduced.

The reduction in the incubation time allows for an automation of the process.

EXAMPLES

The Examples which follow are set forth to aid in the understanding of the invention but are not intended to, and should not be construed to limit the scope of the invention in any way. The Examples do not include detailed descriptions of conventional methods. Such methods are well known to those of ordinary skill in the art.

Example 1

Methods

As in the original Nijmegen assay, test samples are heated for 90 minutes at 58° C. and centrifuged for 10 minutes to destroy residual FVIII.

The coagulation analyzer employed must provide on board ability of three subsequent sample dilution steps and three reagent additions. An application was defined on a Ceveron s100 (Technoclone), as below.

After loading the heat inactivated samples and the normal pool plasma, sequential automated analytical steps occur as follows:

1. Predilution with heat inactivated FVIII/VWF deficient plasma or Owren's Veronal buffer (if needed).

2. Mixing with rFVIII (KOVALTRY®, 1.0 IU/mL).

3. Incubation for 10 minutes at 37° C.

4. Dilution of incubated samples 1:10 with Imidazole buffer, pH 7.3 and analysis for residual rFVIII activity in the absence of VWF using a clotting-based assay.

In addition, a standard reference curve is generated using the 1.0 IU/mL rFVIII as calibrator to translate the second results from the sample measurements into residual FVIII Activity.

| Dilution media | Samples | Sample dilution | rFVIII | residual | BU | BU × dilution | mean | mean EQA result |
|---|---|---|---|---|---|---|---|---|
| Owren's Buffer | 10 BU | 1 | 6.9 | 16.3 | 2.62 | 2.6 | 9.9 | 12 |
| | | 3 | 8.9 | 21.0 | 2.25 | 6.8 | | |
| | | 5 | 12.6 | 29.7 | 1.75 | 8.8 | | |
| | | 10 | 19.7 | 46.4 | 1.11 | 11.1 | | |
| | 5 BU | 1 | 11.5 | 27.1 | 1.88 | 1.9 | 5.6 | 5.3 |
| | | 3 | 16 | 37.7 | 1.41 | 4.2 | | |
| | | 5 | 16.1 | 37.9 | 1.40 | 7.0 | | |
| | 1 BU | 1 | 20.5 | 48.3 | 1.05 | 1.1 | | 1.2 |
| | Control | n.a. | 42.5 | | | | | |
| HI.FVIII.VWF.DP | 10 BU | 1 | 6.9 | 14.6 | 2.78 | 2.8 | 10.4 | 12 |
| | | 3 | 5.7 | 12.1 | 3.05 | 9.2 | | |
| | | 5 | 13.3 | 28.1 | 1.83 | 9.1 | | |
| | | 10 | 21.1 | 44.7 | 1.16 | 11.6 | | |
| | 5 BU | 1 | 11.5 | 24.3 | 2.04 | 2.0 | 5.9 | 5.3 |
| | | 3 | 16 | 33.9 | 1.56 | 4.7 | | |
| | | 5 | 17.4 | 36.8 | 1.44 | 7.2 | | |
| | 1 BU | 1 | 20.5 | 43.4 | 1.20 | 1.2 | | 1.2 |
| | Control | n.a. | 47.3 | | | | | |

Results

Two samples whose inhibitor activities with the original Nijmegen assay were 0 and 14 NBU, were analyzed with the automated method resulting in activities of 0 and 11 NBU respectively. Incubation for 5 and 10 minutes yielded similar results.

CONCLUSION

Rapid, fully automated FVIII-inhibitor testing can be performed with a dedicated coagulation analyzer using rFVIII in a VWF-free matrix. Automation and reduced assay time improve viability and availability of a normally protracted assay, permitting a more rapid and informed clinical response.

What is claimed is:

1. A method of testing for FVIII inhibitors in a patient sample, the method comprising the following steps:
   a. providing a previously obtained patient plasma sample,
   b. providing a buffered normal pool plasma sample,
   c. providing a control plasma sample which is clotting factor VIII (FVIII)/von Willebrand Factor (VWF) deficient,
   d. heat treating the samples provided in steps a) to c),
   e. adding recombinant FVIII (rFVIII) to the control plasma sample,
   f. combining the patient plasma sample and the control plasma sample with rFVIII to obtain a test mixture,
   g. combining the normal pool plasma sample and the control plasma sample with rFVIII to obtain a control mixture,
   h. incubating the test mixture and the control mixture for less than 30 minutes, and
   i. analyzing the mixtures for residual rFVIII activity in the absence of VWF.

2. The method according to claim 1, wherein the control plasma sample is devoid of VWF.

3. The method according to claim 1, wherein the incubation step is carried out for about 15 minutes.

4. The method according to claim 1, wherein the incubation step is carried out for about 10 minutes.

5. The method according to claim 1, wherein the incubation step is carried out for about 5 minutes.

6. The method according to claim 1, wherein the incubation step is carried out at a temperature of about 37° C.

7. The method according to claim 1, wherein the patient plasma sample of step a) is pre-diluted with a buffer agent.

8. The method according to claim 7, wherein the buffer agent is an imidazole buffer, owren's veronal buffer, or saline solution.

9. The method according to claim 7, wherein the incubated samples are diluted in the range of 1:20, 1:10, or 1:5.

10. The method according to claim 1, wherein the normal pool plasma and the control plasma samples are replaced with a buffered agent.

11. The method according to claim 1, wherein the residual rFVIII activity is determined by a clotting assay or a chromogenic assay.

12. The method according to claim 11, wherein the clotting assay is an activated partial thromboplastin time assay (APTT).

13. The method according to claim 12, wherein the clotting assay is performed in the absence of VWF.

14. The method according to claim 1, wherein the method is an automated process.

15. The method according to claim 14, wherein the heat-treated samples of step d) are loaded on a coagulation analyzer.

16. The method according to claim 14, wherein the automated process comprises the following sequential steps:
   a. providing heat-treated samples of a patient plasma, of a normal pool plasma, and of a control plasma with rFVIII,
   b. combining the patient plasma sample and the control plasma sample with rFVIII to obtain a test mixture,
   c. combining the normal pool plasma sample and the control plasma sample with rFVIII to obtain a control mixture,
   d. incubating the test mixture and the control mixture for about 5, 10, or 15 minutes, and
   e. analyzing the mixtures for residual rFVIII activity in the absence of VWF.

17. The method according to claim 14, wherein the control plasma sample is devoid of VWF.

* * * * *